(12) United States Patent
Maev et al.

(10) Patent No.: US 7,775,415 B2
(45) Date of Patent: Aug. 17, 2010

(54) METHOD AND APPARATUS FOR ASSESSING THE QUALITY OF SPOT WELDS

(75) Inventors: Roman Gr. Maev, Windsor (CA);
Frank J Ewasyshyn, Rochester, MI (US); Serguei A Titov, Moscow (RU); John M Paille, Addison Township, MI (US); Elena Yu Maeva, Windsor (CA); Alexey A Denisov, Windsor (CA); Fedar M Seviaryn, Windsor (CA)

(73) Assignee: Chrysler Group LLC, Auburn Hills, MI (US)

( * ) Notice: Subject to any disclaimer, the term of this patent is extended or adjusted under 35 U.S.C. 154(b) by 1099 days.

(21) Appl. No.: 11/151,974

(22) Filed: Jun. 14, 2005

(65) Prior Publication Data

US 2005/0230360 A1 Oct. 20, 2005

Related U.S. Application Data

(63) Continuation of application No. 10/454,350, filed on Jun. 4, 2003.

(51) Int. Cl.
*B23K 31/12* (2006.01)
(52) U.S. Cl. ........................ 228/104; 228/102; 228/103; 228/8; 228/9; 228/56.5; 219/91.1; 73/588; 73/632; 73/641; 73/644
(58) Field of Classification Search .................. 228/102, 228/103, 104, 8, 9, 56.5; 219/91.1; 73/588, 73/632, 641, 644
See application file for complete search history.

(56) References Cited

U.S. PATENT DOCUMENTS

| 4,208,917 | A | 6/1980 | Aoyama et al. |
| 4,265,119 | A | 5/1981 | Dubetz et al. |
| 5,439,157 | A | 8/1995 | Geier et al. |
| 5,507,183 | A | 4/1996 | Larue et al. |
| 5,608,165 | A | 3/1997 | Mozurkewich, Jr. |
| 5,723,791 | A | 3/1998 | Koch et al. |
| 6,072,144 | A | 6/2000 | Perryman |
| 6,116,090 | A | 9/2000 | Maev et al. |
| 6,332,011 | B1 * | 12/2001 | Johnson ...................... 376/249 |
| 6,546,803 | B1 | 4/2003 | Ptchelintsev et al. |
| 6,896,171 | B2 * | 5/2005 | Den Boer et al. ............ 228/103 |
| 6,948,369 | B2 * | 9/2005 | Fleming et al. ................ 73/588 |
| 7,132,617 | B2 * | 11/2006 | Lee et al. ..................... 219/109 |

\* cited by examiner

*Primary Examiner*—Steven Bos
*Assistant Examiner*—Paul A Wartalowicz
(74) *Attorney, Agent, or Firm*—Ralph E. Smith

(57) ABSTRACT

A method and apparatus for evaluating the size and/or quality of a spot weld. The apparatus includes a two-dimensional array of ultrasonic transducers arranged with a delay line for positioning adjacent a surface of a weld. A layer of gel is placed between the delay line and the weld surface. The array of transducers emit ultrasonic waves that pass into the weld. The reflected waves are received by the transducers and relayed to a central processing unit that analyzes the time delay, amplitude, and amplitude attenuation to calculate the border of the weld nugget, the thickness of the welded material, the thickness of the gel layer, and other factors contributing to weld quality.

5 Claims, 4 Drawing Sheets

METHOD AND APPARATUS FOR ASSESSING THE QUALITY OF SPOT WELDS

CROSS-REFERENCE TO RELATED APPLICATIONS

This application is a continuation of pending U.S. patent application Ser. No. 10/454,350, filed Jun. 4, 2003.

STATEMENT REGARDING FEDERALLY SPONSORED RESEARCH

Not applicable.

BACKGROUND OF THE INVENTION

1. Field of the Invention

The invention relates to a method and apparatus for evaluating the quality of a spot weld. More specifically, the invention relates to a method and apparatus for determining the size and quality of a nugget in a spot weld through analysis of ultrasonic waves directed into the weld.

2. Description of Related Art

A conventional spot weld inspecting device, as shown in FIG. 1, comprises a single ultrasonic probe 50, comprising a transducer 52 and a delay line 54 having a delay line surface 56 for direction against a surface being evaluated. The probe 50 transmits an ultrasonic wave into a weld and receives a wave reflected therefrom. The device includes a display that operates to receive a signal from the probe and display a visual representation of the reflected wave.

The structure of a typical spot weld is shown in FIG. 1. In this representation, two metal sheets 100, 200 are connected by a spot weld 300. The area of the spot weld can be classified into three general zones which the ultrasonic wave will intersect:

Zone 1 corresponds to an air gap 10 between the metal sheets;

Zone 2 is the weld nugget 20, the diameter of which is to be measured; and

Zone 3 is a stick weld area 30, wherein the sheets 100, 200 are surface bonded without the metallurgical structure formation found in the weld nugget 20.

The weld nugget 20, zone 2, and the stick weld area 30, zone 3, are substantially transparent to the ultrasonic waves. This is shown in FIG. 1 by the ultrasonic echo responses represented by rays 1, 2, 3. The ultrasonic waves are reflected at any boundary having a change in properties, such as the interface of a metal sheet and the surrounding air. Ray 1, corresponding to zone 1, is completely reflected from the inner face 120 of sheet 100 due to the air gap, whereas rays 2, 3 pass through zones 2, 3 and are not reflected until they reach the opposite face 220 of metal sheet 200.

Referring now to FIG. 2, pulses S11, S21, S31 are a graphical display of the ultrasonic waves represented by rays 1, 2, 3, respectively, as they are reflected to the ultrasonic probe 50 by a respective surface of the metal sheet 100, 200 in the area of the indentation mark 70. Pulse S11 is the first wave reflection of a given ultrasonic pulse transmitted by probe 50. Not all of the reflected pulse returns to the ultrasonic probe 50. Some is reflected back into the metal sheet by the near face 110 of metal sheet 100. Thus, multiple signals will be received for each wave transmitted. In FIG. 2, pulses S12, S13, S14 represent these multiple echoes inside the metal sheet 100. Each echo is time delayed, with the time between echoes $T1=2\,d1/C$, where d1 is a thickness of the metal sheet 100 and C is the sound velocity within the material.

Likewise, pulses S22, S23, and S32, S33 represent subsequent reflections from the opposite face 220 of the spot weld in the area of the weld nugget 20 and stick weld 30 respectively. The periods of these pulses are $T2=T3=2\,(d1+d2)/C$, where d2 is the thickness of the lower sheet. The amplitude of the signals S1, S2, S3 is a decreasing function of time due to attenuation of the signal as it continues to partially reflect within the metal sheets 100, 200. The rate of decay is slightly larger for S2 than for S3 because the grain structure of the nugget 20 results in a greater signal attenuation than is found in the stick weld area.

Thus, if there is a gap between sheets within the cross section of the ultrasound beam it can be easily detected in the time domain. It is only possible to distinguish nugget and stick zone by analysis of the slope of the pulse trains, i.e. the rate of decay of the signal echoes.

When a single transducer covers several zones, the output signal S is a sum of the signals S1, S2, S3 weighted by the factors A1, A2, A3:

$$S = S1\,A1 + S2\,A2 + S3\,A3$$

where A1, A2, A3 are areas of the of the spot weld zone with delamination (air gap 10), weld nugget 20 and stick weld 30, measured in a plane defined between the sheets 100, 200.

Signal S1 can be eliminated from this relationship by time discrimination. The signals S2 and S3 are overlapping in time domain, so it is difficult to estimate S2, i.e. nugget spot weld size. Practically, even a skilled operator can only distinguish the case of very good weld ($A1+A3\approx0$) and the case of very bad weld ($A2\approx0$).

The second general problem comes from the stochastic nature of the weld formation. The boundary between zones with high and low attenuation is smooth therefore it is difficult to predict the position where the weld material becomes strong enough to withstand applied mechanical force. Thus acoustically determined diameter is not necessary coincide with the nugget size obtained from the mechanical destructive test.

To separate responses S2 and S3 it was proposed to employ a ring-shaped probe (U.S. Pat. No. 4,208,917). The outside diameter of the probe is equal to the outside diameter of the electrode tip, and the inside diameter of the probe is equal to the minimum diameter of the weld nugget according to the Spot Welding Standard. Thus if the signal recorded by this probe demonstrates low attenuation it means that the sound travels through the stick weld zone and the nugget diameter is smaller than the minimum size.

Nevertheless the result of the weld test strongly depends upon where the probe was located relative to the weld nugget area. In addition the size of the nugget can not be measured with this technique.

The mechanical scanning systems with single probe (U.S. Pat. No. 4,265,119) or several probes (U.S. Pat. No. 6,116,090) employs the ultrasonic beam with diameter much smaller than the minimum nugget size. These systems are potentially able to detect the boundary between weld nugget 20 and the stick weld area 30 or the air gap 10. Nevertheless, its usage is not convenient for mass production non-destructive testing because of the time-consuming mechanical scanning procedure. In addition, it is necessary to apply an immersion liquid like water instead of an ultrasonic gel for sound coupling. This is difficult when conducting test procedures on tilted or vertical surfaces because of the high fluidity of the immersion liquid.

Electronic scanning using arrays of ultrasonic transducers allows overcoming the problems of the mechanical scanning. An example of an apparatus using this technique is described in U.S. Pat. No. 6,072,144. The disclosed phased array system can produce accurate weld nugget size measurement and employs an immersion water column design and a thin film to hold the immersion liquid. This film is in contact with the weld surface and can be easily destroyed by the roughness of the weld surface. Such limitations are not well suited for a production level test procedure. In addition, the large differential between the acoustic impedance of steel and the immersion liquid considerably reduces the effectiveness of phased arrays.

In the examples mentioned above, the surface of the spot weld is assumed to be a perfect flat surface. It is also assumed that the probes occupy stable, proper position on the metal sheet. However, most real spot welds have irregular curved surfaces on both sides, as shown in FIG. 1, and the metal sheets can be deformed in the vicinity of the spot weld. The real shape of the spot weld and the deformation of the metal sheets are related to the type of welding machine and electrodes, parameters of welding process, electrode tip wear, type and thickness of the welded material and other surface conditions. Thus, the probe can be randomly tilted so that the ultrasonic ray intersects the surfaces at different angles which may not be equal to 90°. This situation is illustrated in FIG. 3, where ray 1 intersects the upper surface of the indentation 70 at angle $\alpha$ and is reflected from the lower surface at angle $\beta$. Due to the irregularity of each surface, the values of these angles will generally be different for every point on the spot weld.

The transmission and reflection coefficients of an ultrasonic ray are sensitive to the tilt of the surface. The amplitude of the response signal received from the particular point depends on the angles $\alpha$, $\beta$. Thus, the amplitude decay is determined by the curvature of the indentation mark, and the attenuation of the sound waves inside the weld as well. The above-described method for nugget and stick weld size estimation, based on the attenuation rates, becomes incorrect when the surfaces are curved.

The gap between the delay line surface 56 and metal surface 110 causes an additional time shift of the reflected signals. Because the signal reflections from the air gap 10 are filtered out on a time-response basis, the varying gap between the probe and the surface 110 can cause confusion in determining the proper time delay. An initial reflection from the surface 110 can be mistaken for a reflection from air gap 10. This could be especially true for a thin sheet 100 and a deep indentation 70.

It would be advantageous to develop a non-destructive testing method of spot welds using an ultrasonic apparatus that displays a proper representation of the weld structure, that is also adaptable for use in a high volume production setting.

BRIEF SUMMARY OF THE INVENTION

The main goal of the invention is development of the spot weld quality evaluation method and device for industrial and production-level conditions. This includes measurement of spot welds with rough and curved indentation marks. The measurement procedure and operation with the device should not require a highly skilled operator and the training course for new operators should be very short.

We propose a 2D Array of Ultrasonic transducers arranged on a surface of the hard delay line. Each element can work as a transmitter and receiver of the ultrasonic waves to test a corresponding area of the spot weld. The opposite side of the delay line is in contact with the surface of the spot weld through a thin layer of ultrasonic gel to provide good acoustical contact. The design of the transducer allows the use of both the hard delay line and water column. A hard delay line is more preferable for industry floor application because the thin film holding the water column is delicate and can be easily torn by the rough surfaces typical to the spot weld.

The size of the array is large enough to cover the maximum spot weld nugget. Each ultrasonic transducer of the array is small enough to produce acoustic beam with angular aperture larger than the possible tilt angle of the rough weld surface. Thus, ultrasound can penetrate into weld in spite of curved indentation surface.

The full data set obtained from all elements of the array is processed to estimate 2D depth profile of the indentation mark at upper and lower surfaces of the sheets. This information is used to compensate for the tilt of the transducer and curvature of the indentation by time shifting of the received signals and dynamically adjusting individual gains for each element. In time domain, this allows separating the pulses reflected from delamination zone between metal sheets and the pulses reflected from front and bottom surfaces.

From estimated 2D depth profile of the indentation the algorithm determines 2D distribution of the tilt angles and compensates for changes in the reflection and transmission coefficients for each element of the array. The distribution of attenuation is then calculated from the slope of the signals reflected from the bottom of the stick and nugget area. To estimate the nugget size, the algorithm evaluates the distribution of S12 amplitudes and attenuation factors across all the elements.

BRIEF DESCRIPTION OF THE SEVERAL VIEWS OF THE DRAWINGS

The present invention will become more fully understood from the detailed description and the accompanying drawings, wherein.

DETAILED DESCRIPTION OF THE INVENTION

Figure 4:
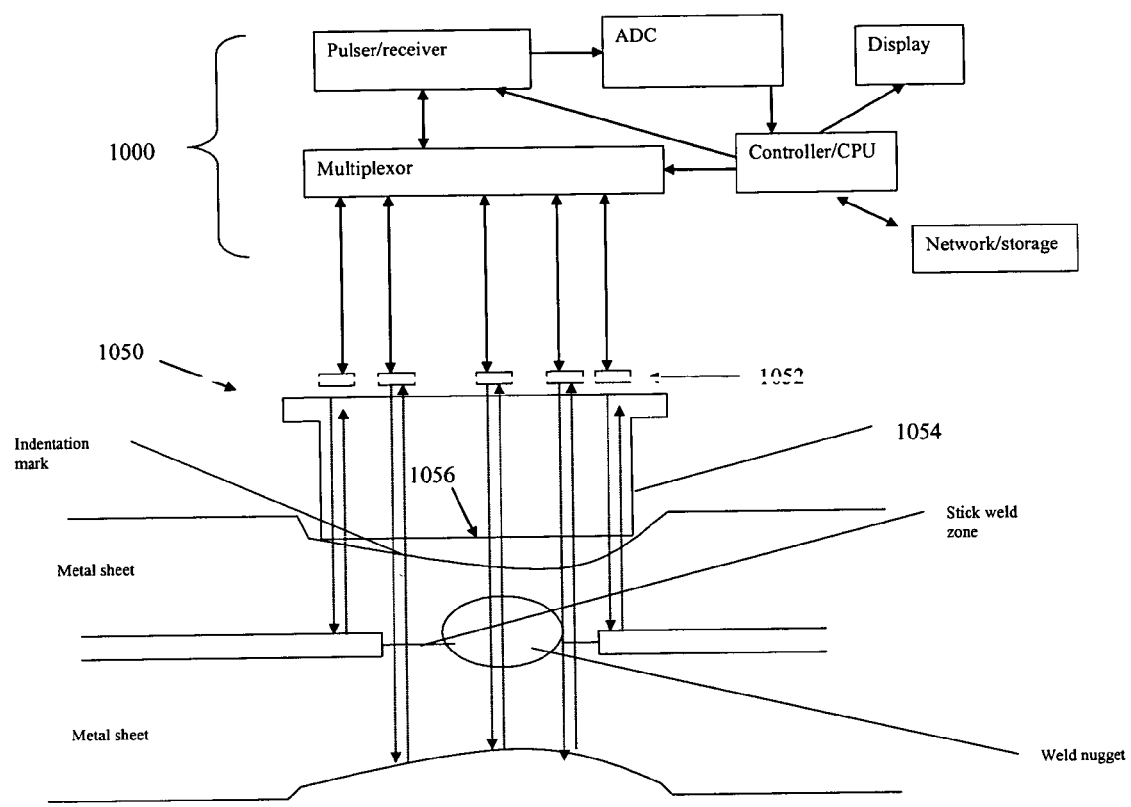
FIG. 4 is a side view of an apparatus for assessing the quality of spot welds according to the invention.

Referring now to FIG. 4, the basis of the system is the hand-held probe 1050 which incorporates a two-dimensional array of ultrasonic transducers 1052 with an attached hard delay line 1054. Detailed descriptions of exemplary two-dimensional arrays can be found in commonly assigned U.S. patent application Ser. No. 10/370,540, filed Feb. 20, 2003, and U.S. Pat. No. 6,546,803, entitled Ultrasonic Array Transducer, both of which are hereby incorporated by reference. Each ultrasonic element of the array 1052 can independently transmit or receive the ultrasonic wave with some frequency. During the test procedure the operator positions the delay line surface 1056 against the surface of the spot weld. The good acoustical contact between the delay line and metal surface of the weld is achieved by ultrasonic gel or other immersion liquid which fills the gap between named surfaces.

The array operation and signal processing is carried out by a control system 1000. The pulser/receiver produces a short electrical pulse at a moment determined by the triggering signal from the controller/CPU. The output of the pulser/receiver is connected to specific elements of the array by the multiplexer, under the direction of the controller/CPU. Excited by the electrical pulse, the transducer produces an ultrasonic wave. This wave propagates through the delay line and immersion, and penetrates into spot weld area. Ultrasonic waves reflected by delaminations, inclusions, or by the bottom surface of the lower sheet, travel back into the transducer and produce electrical signals. These signals come back through the multiplexer to the input of the receiver. After analogue processing (amplification, filtration etc.), the signal is converted to the digital form by the A-D converter and travels to the CPU for further processing in accordance with the invention. This procedure is repeated for each element of the array.

Figure 6:
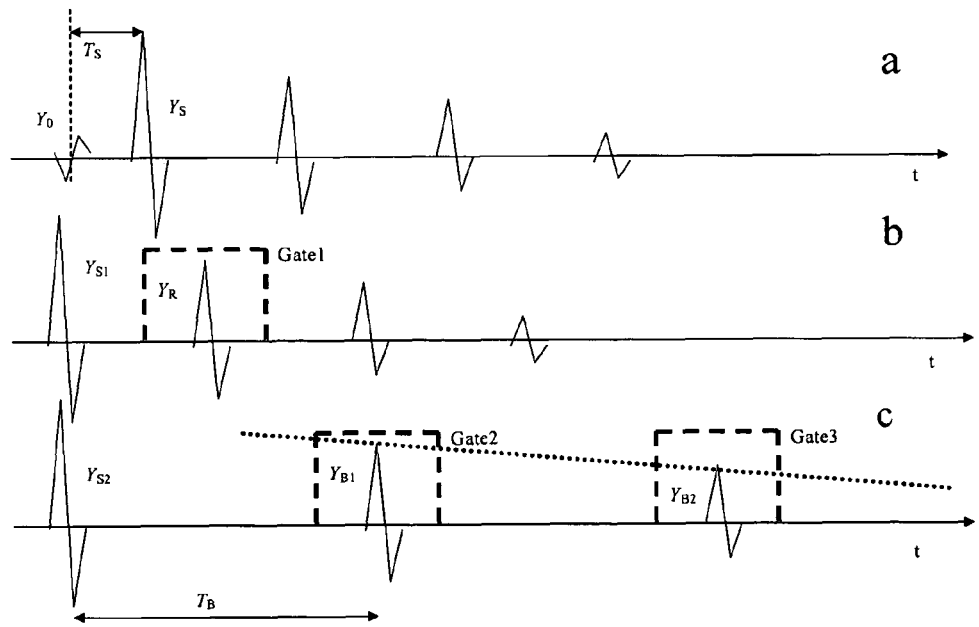
FIG. 6 is a graph showing the signals generated by the apparatus of FIGS. 4-5.

A typical signal series received by an element of the array is schematically shown in FIG. 6a. Pulse Y0 is the wave reflected from the interface between the delay line and gel (or immersion. This pulse is not directly involved in routine signal processing, however it can be used for supplementary analysis, such as detection and exclusion/recalibration of poorly functioning array elements in the matrix. Pulse YS corresponds to the reflection from the surface of the metal sheet. When the thickness of gel layer is small, the YS pulse can be located close to Y0 pulse making it difficult to separate them. However, this is not an obstacle for proposed algorithm since the amplitude of Y0 is always larger compared to that of YS.

The pulses on graph 6a represent the multiple reflections from the internal spot weld structure and reflections from the back surface of the second sheet. The time of flight (TOF), i.e. time delay of the YS pulse relative to the Y0 pulse equals to $$TS=2\,g/c1, \tag{1}$$

where $g$ is the thickness of the gel layer, $c1$ is sound velocity in gel.

Figure 5:
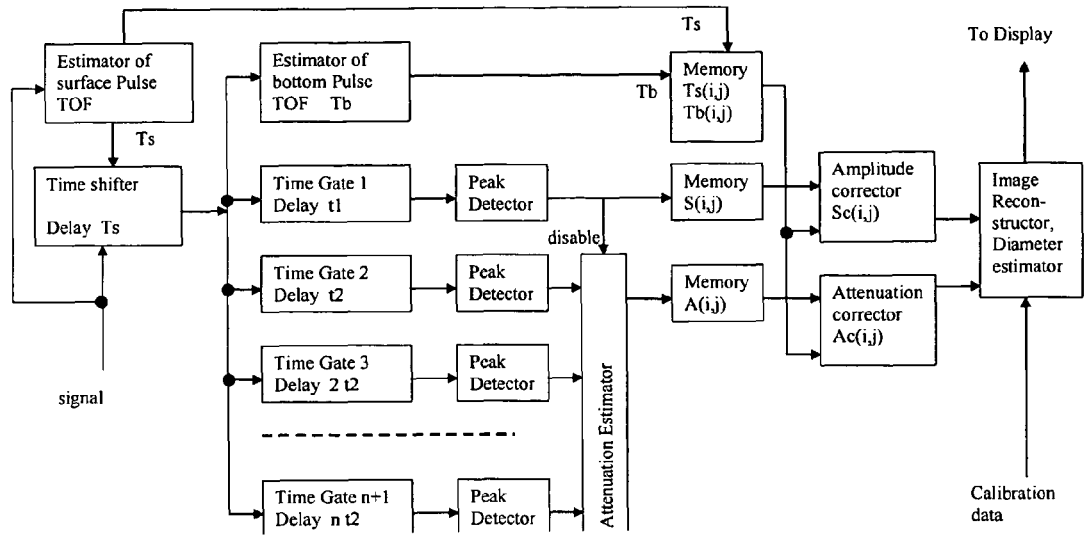
FIG. 5 is a flow chart describing the signal processing algorithm for the apparatus of FIG. 4.

The value of TS varies for different elements of the array because of the tilt of the probe and curvature of the indentation mark. This value is determined by the Estimator of Surface Pulse TOF (see FIG. 5). To compensate this time delay the signal from the element is shifted by $-TS$.

In practice, only relative shifting is important, which means that TS must not necessarily be chosen relative to T0. One can choose to measure time delays relative to signal generation time, excluding T0 peak detector.

The shifted signal with the reflection from the delamination area between sheets is shown in FIG. 6b. Here, YS1 is the pulse reflected from the metal surface, and YR is the first pulse, reflected from the above mentioned delamination. This pulse is selected by the time gate 1 and then its amplitude is evaluated by the peak detector. Nominal delay t1 of the time gate is equal to $t1=2\,d1/c$, where d1 is a thickness of the upper sheet and C is the sound velocity for metal. The range of the gates must is chosen so that it tolerates variations in metal thickness however it must be narrow enough to exclude possibility of detecting surface pulse, its second reflection and reflection from the bottom sheet. The output signal of the peak detector is amplitude S estimated for given element of the array.

The shifted signal of an element located above nugget or stick weld zones is shown in FIG. 6c. Here YS2 is the pulse reflected from the surface, YB1, YB2 ... YBn are the pulses reflected from the bottom of the weld one, two ... n times, correspondingly. These pulses are selected by the gates 2, 3, ..., n+1 and their amplitudes are determined then by the peak detectors. The delays of the gates are $$t2, 2t2, \ldots, nt2, \ldots$$

$$t2=2\,(d1+d2)/C,$$

where $d2$ is the thickness of the lower sheet. Based on number of measured amplitudes an attenuation coefficient A is estimated.

Additionally, the time delay TB of pulse YB1 relative to the pulse YS2 is determined. This value is related to the thickness of the deformed weld $$D=TB/2C. \tag{2}$$

Figure 1:
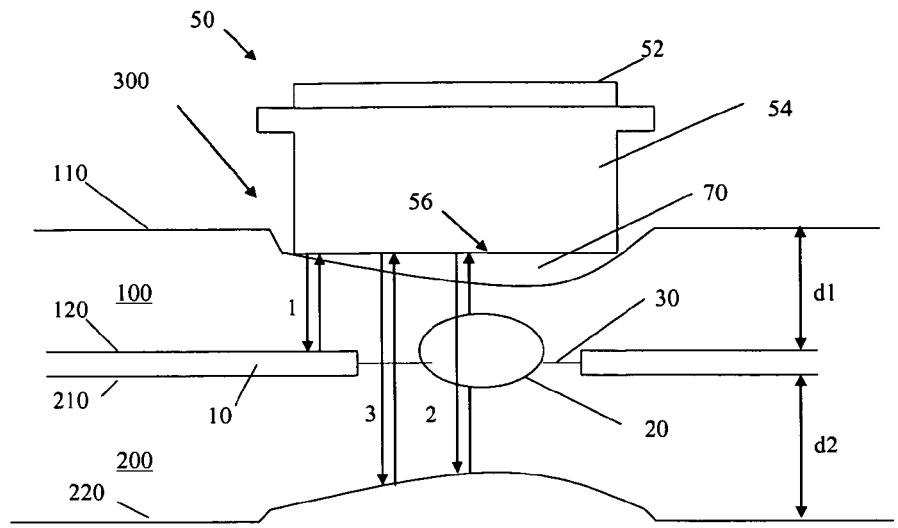
FIG. 1 is a side view of a prior art weld quality assessment apparatus.
Figure 2:
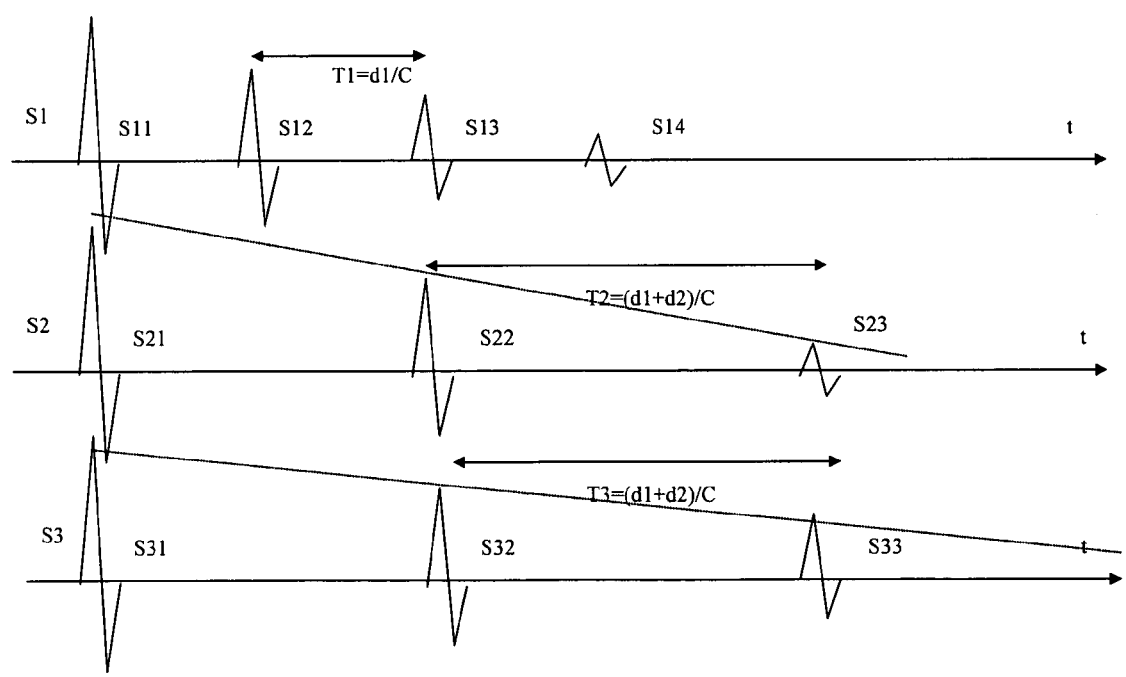
FIG. 2 is a graph of acoustic waves generated by the apparatus of FIG. 1.
Figure 3:
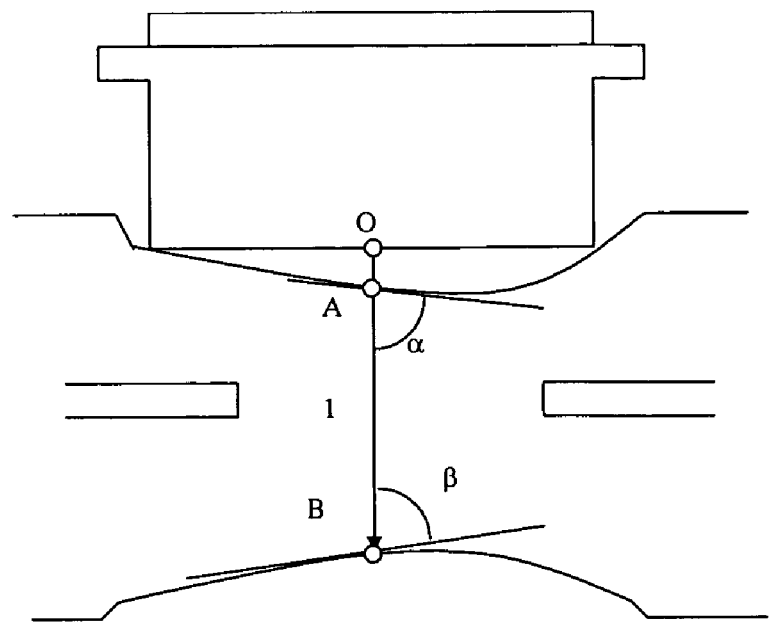
FIG. 3 is a further side view of the prior art apparatus of FIG. 1.

This thickness of the deformed weld is shown in FIG. 3, and is equal to the distance AB for the reflected ultrasonic wave.

The readings and responses are recorded for each element in the array as it is passed over the weld. Positions on the weld surface are located by a coordinate system wherein a given point is identified by the coordinates (i,j). All the measured parameters TS(i,j), TB(i,j), S(i,j), A(i,j) are thus stored in memory. According to formulae (1), (2) the gel thickness g(i,j) and weld thickness D(i,j) in the nugget and stick zone are determined.

The 2D data sets g(i,j) and D(i,j) are used to correct the measured amplitude S(i,j) and attenuation coefficient A(i,j). The algorithm of the correction can be derived from theoretical consideration, numerical simulation, or from results of an experimental investigation including neural network technique.

Figure 7:
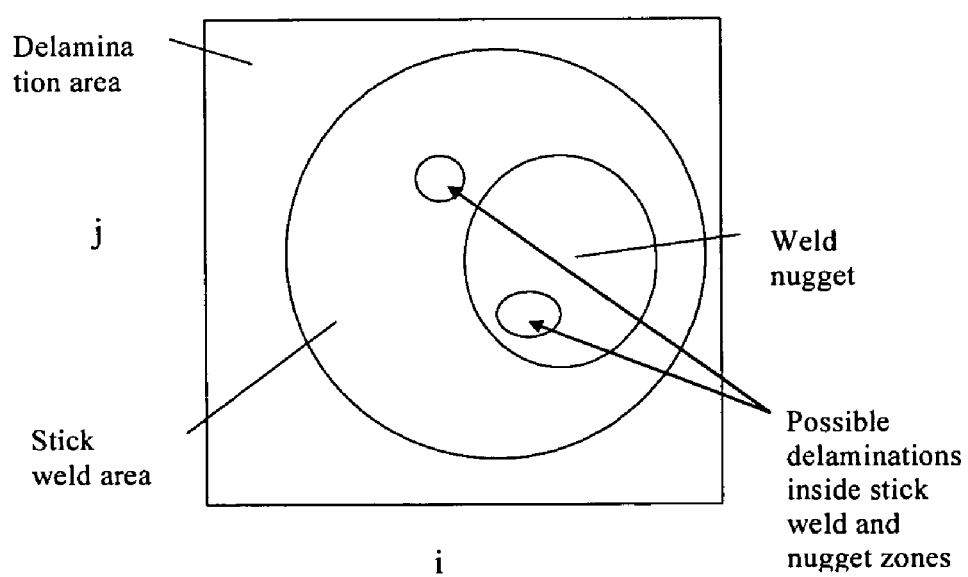
FIG. 7 is a weld map generated by the apparatus of FIGS. 4-6.

The corrected amplitude spatial distribution SC(i,j) is then presented as an image on the display that shows the external delamination area of the weld and internal possible defects such as cracks, voids, or inclusions, as shown in FIG. 7. Continuous repetition of the survey more than 3 times per second creates a live image of the weld. Observing this image, the operator can adjust a position of the probe to be sure that the probe acquires data of interest from the entire weld area.

Nugget weld zone is then determined as a collection of points (i,j) where the corrected attenuation coefficient is larger than a threshold AC>A0 and the amplitude SC=0. Because the attenuation in the weld nugget is greater than in the stick weld zone, the points where AC<A0 and SC=0 corresponds to the stick weld zone. The average diameter of the nugget can be estimated visually by the operator, or with image processing, computer vision, neural network, and other algorithms.

The relationship between visual and actual sizes as well as threshold A0 depends on metal sheet thickness, electrode diameter, kind of the metal and coating. These calibration relationships are estimated in advance by comparing ultrasonic images with results of the actual destructive tests of welds.

The final assessment of weld quality, i.e. whether a weld is satisfactory for its intended purpose, is reached by taking into consideration the corrected nugget size, maximum depth of the indentation marks, and the size of suspected areas of delamination (inclusions, cracks and so on) inside the nugget and stick weld zones. This decision can be made automatically by comparing the obtained results with existing spot weld standards or destructive testing.

The final readings can be streamed via a network to a host server for storage, and can be fed back to welder controls to improve quality control. Additionally, the necessary calibration data can be downloaded to the device through the network or recall from the controller memory or input manually.

While the invention has been described in the specification and illustrated in the drawings with reference to a preferred embodiment, it will be understood by those skilled in the art that various changes may be made and equivalents may be substituted for elements thereof without departing from the scope of the invention as defined in the claims. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the scope of the appended claims.

What is claimed is:

1. A method for assessing quality of a spot weld, the method comprising:
   placing an acoustic probe having a plurality of ultrasonic transducers arranged in a two-dimensional array on a spot weld under test;
   generating a series of ultrasonic signals via the two dimensional array toward the spot weld and analyzing responses therefrom to measure two dimensional profiles of front and back indentation marks of the spot weld;
   correcting the responses in accordance with the profiles;
   recognizing a subset of the responses as being reflected from delamination areas inside and/or in the vicinity of the spot weld and separating the subset from a remainder of the responses;
   measuring an attenuation factor for each of the remainder of the responses;
   recognizing a stick weld area and a weld nugget area using the measured attenuation factors; and
   presenting a two dimensional image of delamination, stick weld and weld nugget areas of the spot weld.

2. The method of claim 1 further comprising:
   generating calibration data relating acoustic image sizes of spot weld nuggets with corresponding actual weld nugget sizes; and
   correcting two dimensional image of the weld nugget area of the spot weld under test using the calibration data.

3. The method of claim 2 wherein the calibration data is generated from destructive testing of a preselected plurality of spot welds.

4. The method of claim 1 further comprising:
   adjusting a position of the acoustic probe and repeating the method.

5. The method of claim 1 further comprising:
   estimating weld quality as a function of size of the weld nugget, presence and size of any delamination zone inside the weld nugget, and depths and profiles of the front and back indentation marks.

* * * * *